United States Patent

Hatfield

[11] Patent Number: 6,117,393
[45] Date of Patent: Sep. 12, 2000

[54] MULTILAYERED GAS SENSOR

[75] Inventor: Thomas N. Hatfield, Mishawaka, Ind.

[73] Assignee: CTS Corporation, Elkhart, Ind.

[21] Appl. No.: 08/783,857

[22] Filed: Jan. 16, 1997

[51] Int. Cl.$^7$ .................................................. G01N 27/16
[52] U.S. Cl. ............................ 422/95; 422/90; 422/94; 422/96; 422/97; 422/98; 73/31.06
[58] Field of Search ................................ 422/90, 94–98; 73/31.06

[56] References Cited

U.S. PATENT DOCUMENTS

| | | | |
|---|---|---|---|
| Re. 33,980 | 6/1992 | Matsuura et al. | 422/98 |
| 3,564,474 | 2/1971 | Firth et al. | 422/97 X |
| 3,883,307 | 5/1975 | Kim | 422/97 |
| 3,959,764 | 5/1976 | Allman | 422/90 X |
| 4,045,177 | 8/1977 | McNally | 23/254 E |
| 4,164,539 | 8/1979 | Johnston | 422/97 X |
| 4,303,612 | 12/1981 | Sonley | 422/94 |
| 4,322,383 | 3/1982 | Yasuda et al. | 422/95 |
| 4,421,720 | 12/1983 | Kamiya et al. | 422/97 |
| 4,447,397 | 5/1984 | Anouchi et al. | 422/94 |
| 4,457,954 | 7/1984 | Dabill et al. | 422/98 X |
| 4,957,705 | 9/1990 | Uchikawa | 422/94 |
| 5,445,796 | 8/1995 | Mori | 422/98 |

FOREIGN PATENT DOCUMENTS

| | | |
|---|---|---|
| 311964 | 4/1989 | European Pat. Off. . |
| 4001048 | 7/1991 | Germany . |
| 52-49095 | 4/1977 | Japan . |
| 54-36997 | 3/1979 | Japan . |
| 54-139598 | 10/1979 | Japan . |
| 54-139599 | 10/1979 | Japan . |
| 55-65149 | 5/1980 | Japan . |
| 55-126851 | 10/1980 | Japan . |
| 55-149834 | 11/1980 | Japan . |
| 58-196448 | 11/1983 | Japan . |
| 63-128249 | 5/1988 | Japan . |
| 1-119755 | 5/1989 | Japan ..................... 422/98 |
| 1-265149 | 10/1989 | Japan . |
| 1540212 | 2/1979 | United Kingdom . |
| 2238617 | 6/1991 | United Kingdom . |

*Primary Examiner*—Arlen Soderquist
*Attorney, Agent, or Firm*—Michael W. Starkweather; Daniel Tychonevich

[57] ABSTRACT

A multilayered gas sensor for detecting the presence of gases in air. In particular, sensors are described for sensing hydrocarbons and nitrogen oxides. An additional feature of the invention is to provide a device that is suitable for sensing gases in the harsh environment of an automobile exhaust system. The device features a ceramic substrate and a glass layer to adhere a catalyst support to the substrate. A catalyst layer of either platinum or rhodium is deposited on the catalyst support and a thermally sensitive resistor element detects reactions of hydrocarbons or nitrogen oxides on the corresponding catalyst.

20 Claims, 2 Drawing Sheets

MULTILAYERED GAS SENSOR

BACKGROUND OF THE INVENTION

1. Field of the Invention

This invention relates to a sensor for detecting the presence of gases in air, and more specifically to a sensor having a multilayered structure for adhering a catalyst over a resistive sensing element.

2. Description of the Related Art

The use of catalysts to enhance the rate of chemical reactions is well known. A catalyst can be any substance that affects a chemical reaction rate without itself being consumed or undergoing a chemical change in the process. Catalysts may be inorganic, organic, or a complex composition of organic groups and metal halides.

The present invention is directed at the use of a catalyst in gas sensors. Catalytic gas sensors function by creating a chemical reaction when the gas to be sensed comes in contact with the catalyst. Often, the chemical reaction creates a temperature change that can be used to effect the electrical resistance of a conductor. Thus, typical sensing elements are conductors that both exhibit conductivity changes as the temperature varies and are coated with a catalyst.

Typically, gas sensing devices use both a catalyzed sensor and a non-catalyzed reference sensor. The two sensors are typically coupled in a Wheatstone bridge arrangement. Gas concentrations can be determined by measuring the difference in voltage drop across the catalyzed and non-catalyzed coated conductors.

3. Related Art

Examples of patents that are related to the present invention are as follows, and each patent is herein incorporated by reference for the supporting teachings:

U.S. Pat. No. 4,045,177, is an apparatus for detecting combustible gases.

U.S. Pat. No. 4,322,383, is a gas component detection device composed of two metal oxide sensors.

U.S. Pat. No. 4,447,397, is a catalytic gas sensor having a filament coated with titanium dioxide ($TiO_2$).

U.S. Pat. No. 4,957,705, is an oxygen gas concentration detecting device.

U.S. Pat. No. 5,445,796, is an oxygen concentrating sensor with a heat resistant coating.

U.S. Pat. No. Re. 33,980, is a thick film gas sensitive element.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singularly or when considered in combination, applicant's claimed invention.

4. Problems with Related Art

A problem with current gas sensors is that there is no compact, cost effective, and durable hydrocarbon or nitrogen oxide sensors that is suitable for functioning in the harsh environment of an automobile exhaust system. Sensors are needed to measure these gases to assure that automobiles are complying with emission requirements. The auto industry currently uses oxygen sensors to indirectly measure hydrocarbons and nitrogen oxides, but indirect measurement is not as accurate as more direct measurement.

A further problem is the difficulty in designing a sensor structure that can operate properly when exposed to temperature extremes, continuous vibrations, mechanical shock and contaminants without experiencing a significant degradation of performance over its expected life.

It is noted that the above described problems, and other problems are solved through the subject invention and will become more apparent to one skilled in the art, from the detailed description of the subject invention.

SUMMARY OF THE INVENTION

It is a feature of the invention to provide a multilayered sensor for directly detecting the presence of gases in air. In particular, the sensor directly senses hydrocarbons and nitrogen oxides by using a thermally sensitive resistor that responds to the reaction of the gases on a catalyst.

An additional feature of the invention is to provide a cost effective device that is suitable for sensing gases in a harsh environment of an automobile exhaust system.

The structure of the gas sensor includes a base with a resistor element. The electrical resistance of the resistor element changes as the temperature varies. A layer of glass material is located on the base over the resistor element, and a catalytic support structure is adhered onto the layer of glass. On the catalytic support structure a catalyst is deposited that will promote an exothermic reaction when contacting the gas to be sensed. The exothermic reaction causes a rise in the temperature of the resistor element.

A further feature of the invention is to provide a device that has a ceramic substrate and a glass layer for adhering a catalyst support layer to the substrate. The catalyst support structure is comprised of high surface area ceramic particles. A catalytic material is deposited on the catalytic support structure for reacting with the gas to be sensed.

The invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and so that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Figure 1:
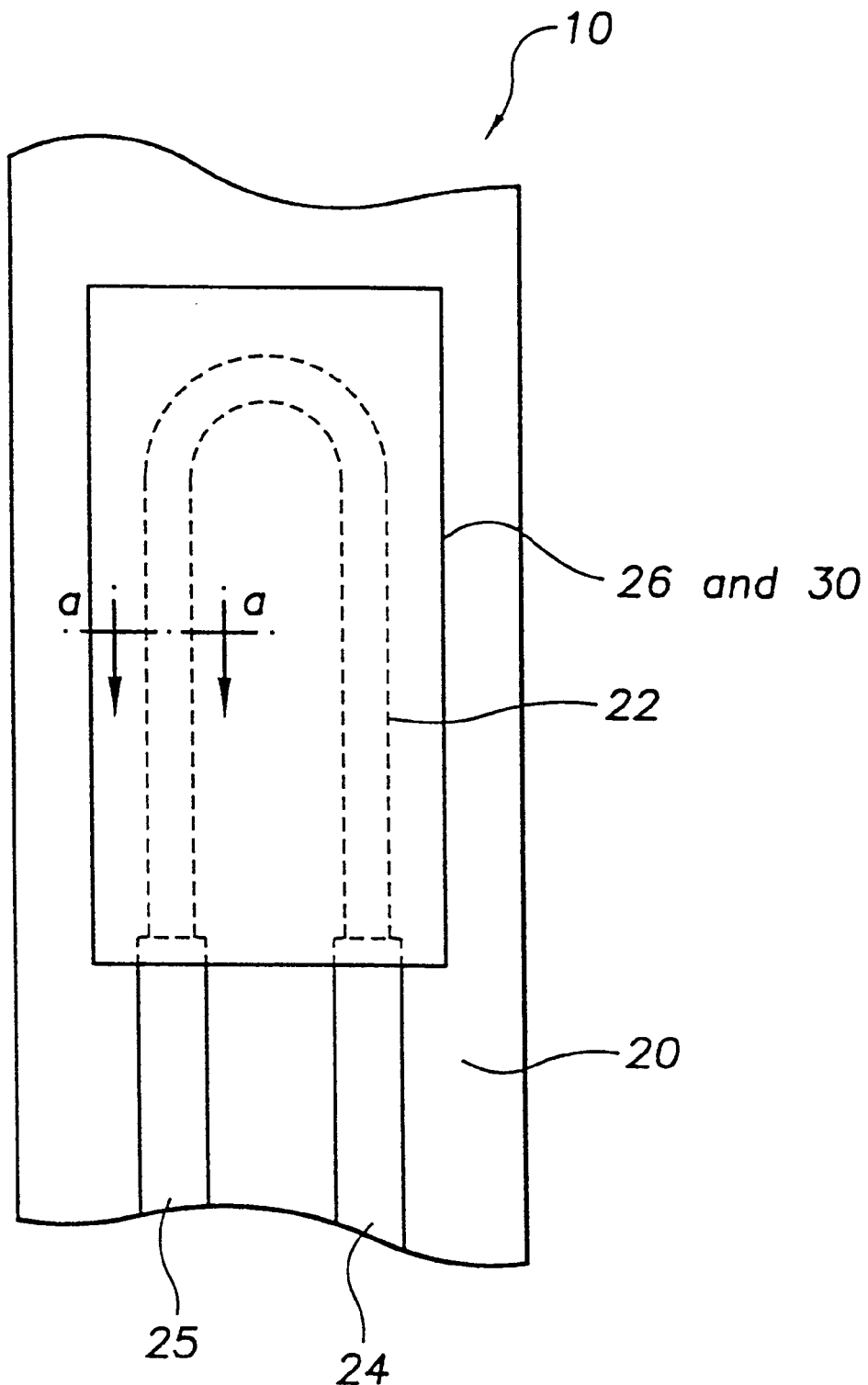
FIG. 1 is a plan view showing the sensor of the present invention.

It is noted that the drawings of the invention are not to scale. The drawings are merely schematic representations, not intended to portray specific parameters of the invention.

The drawings are intended to depict only typical embodiments of the invention, and therefore should not be considered as limiting the scope of the invention. In the drawings, like numbering represents like elements between the drawings.

DETAILED DESCRIPTION OF THE PREFERRED EMBODIMENT

The present invention provides a gas sensor having a multilayered structure. The structure is ideally suited to sensing hydrocarbons and nitrogen oxides in an automobile exhaust system. Regarding FIG. 1, there is a plan view of the gas sensor 10 of the present invention showing a portion of a substrate (base) 20. Substrate 20 is preferably made out of a ceramic material but other suitable dielectric materials may be utilized. Only the portion of substrate 20 containing a catalytic support structure 30 and glass adhesion layer 26 has been included in FIG. 1.

The remaining portion of substrate 20 can take on any desired configuration that will supply the necessary structural and thermal properties for the sensor. For instance, the structure must be strong enough to survive the shock and vibration attendant in an automobile exhaust system. In addition, the thermal properties must be such that any catalytic reactions occurring on catalytic support structure 30 can be detected by a thermally sensitive resistor element 22 located on substrate 20 (i.e. the substrate must not extract so much heat from the catalytic reaction that there is no resulting temperature increase in resistor element 22).

Located on substrate 20 and electrically connected to resistor element 22, are conductors 24 and 25. Conductors 24 and 25 are connected to circuitry (not shown) that can detect resistance changes from accompanying voltage drops along the length of resistor element 22.

Figure 2:
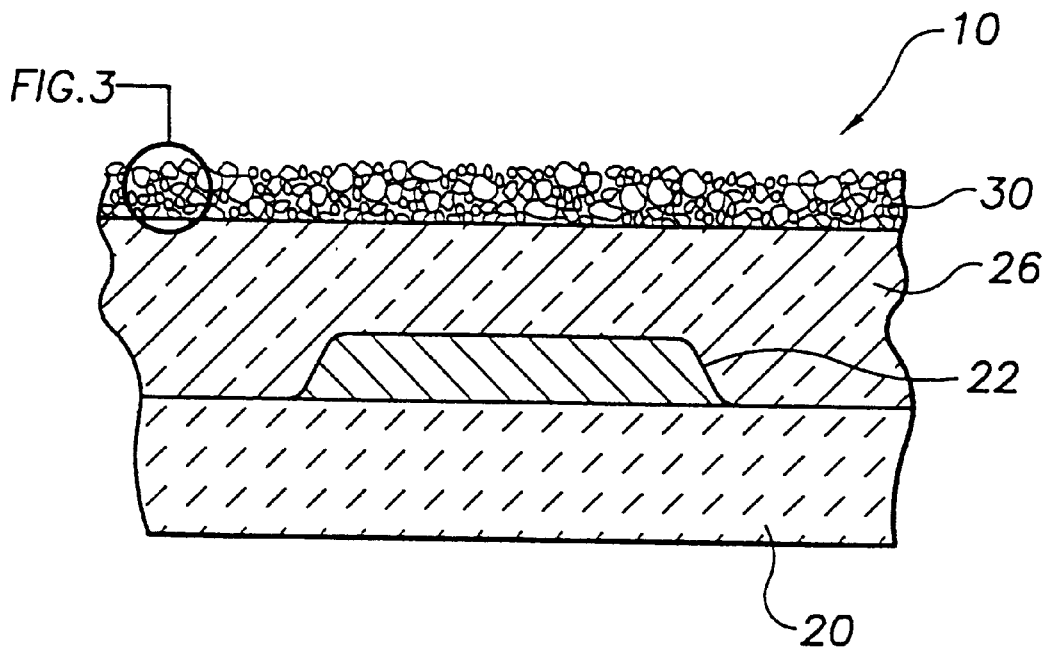
FIG. 2 is a cross-section of FIG. 1 taken through section a—a showing the multilayered structure.

In FIG. 2, a cross section taken through resistor element 22 is depicted. Resistor element 22 can be deposited on substrate 20 using any conventional thick or thin film technique as long as the deposit is robust enough to withstand the environment of an auto exhaust system and the thermal coefficient of resistivity is high enough so that the resistor will respond to temperature changes from catalytic reactions. The material used to form resistor element 22 can be selected using these same criteria. In the preferred embodiment, it was found that platinum is a suitable material for resistor element 22 and that screen printing proved to be a suitable deposition method.

Conductors 24 and 25 can likewise be deposited using any conventional thick or thin film technique. Gold was selected as the conductor material for the preferred embodiment.

A layer of glass 26 is deposited over the resistor element 22. One way of forming glass layer 26 is to mix powdered glass with a screening agent comprised of an organic solvent, a rheology agent and a wetting agent. This creates a paste that can be screen printed on the substrate. The glass layer can also be formed using a doctor blade or brushing the mixture on. The layer of glass 26 is then dried but not fired yet. This provides a firm surface on which to deposit the catalytic support structure 30, but still enables the glass to act as an adhesion promoter when the structure is subsequently fired.

The catalytic support structure 30 is comprised of high surface area particles such as powdered alumina. The particles can be calcined before applying them to the sensor structure to help assure that they have a high surface area for receiving a catalyst coating. The alumina particles can be combined with aluminum hydroxide or a similar substance to form a paste for application. The paste can be applied with thick film techniques such as screen printing.

After catalytic support structure 30 is applied the entire assembly is fired at the proper firing profile for the glass employed. This will reflow the glass and cause it to firmly adhere to both the alumina particles and substrate 20. It is important that the glass bond very firmly to both the substrate and catalytic support because if the alumina particles flake off, the sensor will no longer function. In principal, any glass film formation, including many commercially available varieties such as GA-4 from Nippon Electric Glass, can be used as described above, provided it has the property of adhering to both substrate 20 and the catalytic support structure 30. A temperature of 700 degrees centigrade for 1 hour is sufficient to reflow the GA-4 glass.

The final step is to apply a catalyst to catalytic support structure 30. In the preferred embodiment for a hydrocarbon sensor, platinum is used for the catalyst. The platinum is applied as a chloroplatinic acid solution using a dropper or other suitable technique. Afterwards the entire structure is again fired at about 500 degrees centigrade for 1 hour to reduce the acid to platinum.

Figure 3:
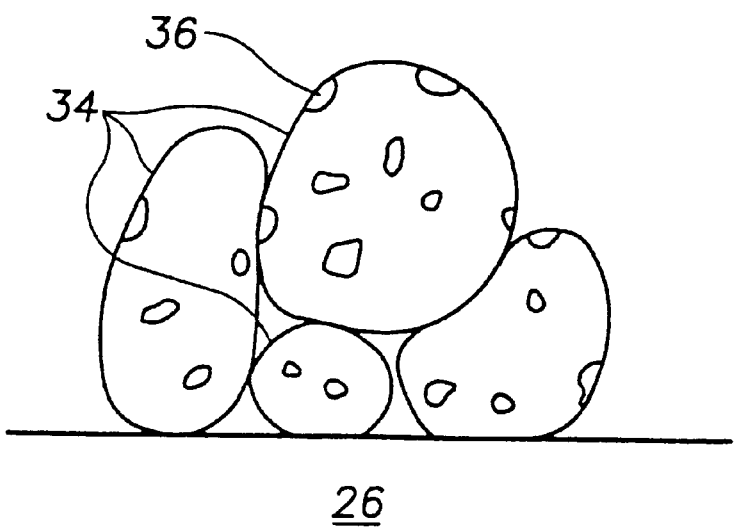
FIG. 3 is an enlargement of a portion of FIG. 2 showing the catalyst support structure.

The final catalytic support structure, as shown by the enlarged view in FIG. 3, is comprised of alumina particles 34 adhered to glass layer 26. The particles vary in size and shape and the surface may include pores 36. When the chloroplatinic acid is applied and dried as described above, the surfaces of particles 34, including the surfaces of pores 36, will be covered by a very fine layer of platinum.

Operation of the Sensor

The key to the operation of the sensor is the catalytic reaction of the gas to be sensed and the ability of the resistor element to respond to this respond to the reaction by a resulting change in its resistance. For example, as a hydrocarbon gas comes in contact with the platinum catalyst, a chemical reaction occurs in which the hydrocarbon is combusted and heat is generated. The greater the quantity of hydrocarbons, the more heat is produced, thus causing the resistance of resistor element 22 to rise accordingly.

The resistance of resistor element 22 is then compared to the resistance of a reference sensor (not shown), which is in the same environment, but is not covered with a catalyst. The difference in the resistance between resistor element 22 and the reference sensor is due to the heat generated by the catalytic reaction and indicates the concentration of hydrocarbons in an exhaust stream.

Nitrogen Oxide Sensor Variation

A nitrogen oxide sensor can be made using the same procedure as outlined above for a hydrocarbon sensor except that a rhodium catalyst is substituted for platinum. The rhodium is deposited onto the catalytic support structure 30 in the form of rhodium chloride. The rhodium chloride is deposited in the same manner as the chloroplatinic acid and likewise fired to reduce the solution to pure rhodium.

Variations of the Preferred Embodiment

Although the illustrated embodiments depict the resistor element 22 in a horseshoe configuration one skilled in the art will realize that the preferred embodiment would work with most any pattern. The horseshoe shape merely provides an efficient means to place electrical conductors 24 and 25 in close proximity to each other for size constraints and manufacturability reasons.

In addition, the glass layer 25 and catalytic support structure 30 do not have to be applied in a rectangular shape as depicted in FIG. 1. They can be deposited in any desired shape. As discussed above, substrate 20 can also take on other configurations. Furthermore, the glass and ceramic particles can be mixed with water or other suitable solutions/ solvents to form a paste for application to the base.

Furthermore, other types of ceramic particles besides alumina can be used in the catalytic support structure, and other glass materials besides GA-4 would also be suitable. Any glass that will adhere firmly to both the ceramic particles and substrate can be used.

While the disclosure discusses the sensing of both hydrocarbon gas and nitrogen oxide, one skilled in the art of making gas sensors would easily adapt this design to sense most any gas that is capable of an exothermic reaction upon being exposed to a suitable catalytic material placed over the catalytic support structure.

Although the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A method for manufacturing a multilayered gas sensor, comprising:
    a) supplying a base with a thermally sensitive resistor element thereon,
    b) applying a glass layer to the base;
    c) drying the glass layer;
    d) applying a porous catalyst support structure on the glass layer;
    e) heating the base, glass layer, and catalyst support structure at a temperature that will both reflow and adhere the glass layer to the catalyst support structure and the base; and
    f) applying a catalyst onto exposed surfaces of the catalyst support structure after step e).

2. The method of claim 1, wherein the base is comprised of ceramic.

3. The method of claim 2, wherein the ceramic includes alumina.

4. The method of claim 1, wherein the catalyst support structure is comprised of ceramic particles.

5. The method of claim 4, wherein the ceramic particles comprise alumina having a high surface area.

6. The method of claim 4, wherein the ceramic particles are mixed with aluminum hydroxide to form a paste before application to the base.

7. The method of claim 5, wherein the alumina particles are calcined prior to being applied to the base.

8. The method of claim 1 wherein the catalyst is platinum for initiating reactions with hydrocarbons.

9. The method of claim 1, wherein the catalyst is rhodium for initiating reactions with nitrogen oxides.

10. The method of claim 1, further comprising, supplying the base with conductors electrically connected to the thermally sensitive resistor element.

11. The method of claim 10, wherein the conductors are comprised of gold.

12. The method of claim 1, wherein the glass layer comprises powdered glass.

13. The method of claim 1, wherein the glass layer comprises powdered glass mixed with a screening agent to form a paste.

14. The method of claim 1, wherein the catalyst support structure and glass layer are applied by screen printing.

15. The method of claim 1, wherein the heating temperature for reflowing the glass layer is 700 degrees centigrade.

16. A method for manufacturing a multilayered gas sensor, comprising:
    a) supplying a base having a gold conductor electrically connected to a thermally sensitive resistor element thereon;
    b) making a glass paste using powdered glass mixed with a screening agent;
    c) screen printing the glass paste on the base over the thermally sensitive resistor element;
    d) drying the glass paste to form a glass layer;
    e) calcining porous alumina particles at 600 degrees centigrade for one hour for the purpose of assuring a high surface area;
    f) mixing the alumina particles with aluminum hydroxide to form an alumina paste;
    g) screen printing the alumina paste over the glass layer to form a catalytic support structure;
    h) heating the base, glass layer and catalytic support structure together at a temperature of 700 degrees centigrade to reflow and adhere the glass layer to the alumina particles and the base;
    i) applying a catalyst mixture onto exposed surfaces of the catalytic support structure; and
    j) reheating the base, glass layer, and catalyst support structure at 500 degrees centigrade to reduce the catalyst mixture to a pure catalyst.

17. The method of claim 16, wherein the catalyst mixture is platinic acid.

18. The method of claim 16, wherein the catalyst mixture is rhodium chloride.

19. The method of claim 16, wherein the pure catalyst is platinum for reacting with hydrocarbons.

20. The method of claim 16, wherein the pure catalyst is rhodium for reacting with nitrogen oxides.

* * * * *